(12) United States Patent
Lee et al.

(10) Patent No.: US 7,833,710 B2
(45) Date of Patent: Nov. 16, 2010

(54) POLYNUCLEOTIDE ASSOCIATED WITH BREAST CANCER COMPRISING SINGLE NUCLEOTIDE POLYMORPHISM, MICROARRAY AND DIAGNOSTIC KIT COMPRISING THE SAME AND METHOD FOR DIAGNOSING BREAST CANCER USING THE SAME

(75) Inventors: Yeon-Su Lee, Goyangi-si (KR); Kyung-Hee Park, Seoul (KR); Jae-Heup Kim, Seoul (KR); Kyusang Lee, Suwon-si (KR); Yeon-a Park, Yongin-si (KR); Ji-Young Cho, Suwon-si (KR); Ok-ryul Song, Seoul (KR); Tae-jin Ahn, Seoul (KR); Ok-kyoung Son, Seoul (KR)

(73) Assignee: Samsung Electronics Co., Ltd. (KR)

( * ) Notice: Subject to any disclaimer, the term of this patent is extended or adjusted under 35 U.S.C. 154(b) by 497 days.

(21) Appl. No.: 11/329,299

(22) Filed: Jan. 10, 2006

(65) Prior Publication Data

US 2006/0183139 A1   Aug. 17, 2006

(30) Foreign Application Priority Data

Feb. 14, 2005 (KR) ...................... 10-2005-0012038

(51) Int. Cl.
- *C12Q 1/68* (2006.01)
- *C12P 19/34* (2006.01)
- *C07H 21/02* (2006.01)
- *C07H 21/04* (2006.01)

(52) U.S. Cl. .................. 435/6; 435/91.1; 536/23.1; 536/24.3

(58) Field of Classification Search .................. None
See application file for complete search history.

(56) References Cited

FOREIGN PATENT DOCUMENTS

| WO | 9605306 | | 2/1996 |
|---|---|---|---|
| WO | 9605306 | A2 | 2/1996 |
| WO | 01/77384 | A2 | 10/2001 |
| WO | 2004028346 | A2 | 4/2004 |

OTHER PUBLICATIONS

Cox et al; 2006; Breast Cancer Research, vol. 9, No. 1, pp. 1-5.*
Hegele Arterioscler. Thromb. Vasc. Biol.; 2002, vol. 22, pp. 156-1061.*
Lucentini The Scientist; 2004, vol. 24, p. 20.*
Horner et al; "Breast Cancer Rates by Age" SEER Cancer Statistics Review, 1975-2006; NCI 2008.*
Ren, Z., et al.; "Genetic Polymorphisms in the Human Growth Hormone-1 Gene (GH1) and the Risk of Breast Carcinoma"; Cancer; vol. 101, No. 2; pp. 251-257; Jul. 15, 2004.
Kadouri, L., et al.; "A single-nucleotide polymorphism in the RAD51 gene modifies breast cancer risk in BRCA2 carriers, but not in BCRA1 carriers or noncarriers"; British Journal of Cancer; vol. 90; pp. 2002-2005; 2004.
Tower, G.B., et al.; "The 2G single nucleotide polymorphism (SNP) in the MMP-1 promoter contributes to high levels of MMP-1 transcription in MCF-7/ADR breast cancer cells"; Breast Cancer Research and Treatment; vol. 82; pp. 75-82; 2003.
Mimori, K., et al.; "A Single-Nucleotide Polymorphism of SMARCB1 in Human Breast Cancers"; Genomics; vol. 80, No. 3; pp. 254-258; Sep. 2002.
International Search Report dated May 17, 2006 for Application No. PCT/KR2006/000505 (All references cited in Search Report are listed above).
Written Opinion dated May 17, 2006 for Application No. PCT/KR2006/000505.
Wu and Wallace, Genomics 4, 560 (1989).
Landegren, etc., Science 241, 1077 (1988).
Kwoh, etc., Proc. Natl. Acad. Sci. USA 86, 1173 (1989).
Guatelli, etc., Proc. Natl. Acad. Sci. USA 87, 1874 (1990).
Gusella, Ann. Rev. Biochem. 55. 831-854 (1986).
Nielsen et al., Science 254, 1497-1500 (1991).
J. Sambrook, et al.; "Molecular Cloning: A Laboratory Manual"; Cold Spring Harbor Press, Second Edition, pp. 13.1-13.20, 1989.
EP Extended Search Report; Application No. EP 06715956.6 (EP regional application of PCT/2006000505) dated Jun. 8, 2009.
EPO Communication dated Apr. 11, 2009 citing database documents of accession Nos. ABF99372 and ABF99373.
Kadouri et al., "A single-nucleotide polymorphism in the RAD51 gene modifies breast cancer risk in BRCA2 carriers, but not in BRCA1 carriers or noncarriers," British Journal of Cancer, 2004, vol. 90, No. 10, pp. 2002-2005.
Mimori, et al. "A Single-Nucleotide Polymorphism of SMARCB1 in Human Breast Cancers," Genomics, 2002, vol. 80, No. 3, pp. 254-258.
Ren et al., "Genetic Polymorphisms in the Human Growth Hormone-1 Gene (GH1) and the Risk of Breast Carcinoma," Cancer, 2004, vol. 101, No. 2, pp. 251-257.
Tower et al., "The 2G single nucleotide polymorphism (SNP) in the MMP-1 promoter contributes to high levels of MMP-1 transcription in the MCF-7/ADR breast cancer cells," Breast Cancer Research and Treatment, 2003, vol. 82, No. 2, pp. 75-82.
XP002526198 "*Homo sapiens* chromosome 19 clone RP11-294120 map 19, working draft sequence," retrieved from EBI accession No. EMBL: AC023583, (Feb. 16, 2000).
XP002526199 "*Homo sapiens* chromosome 19 clone CTD-3195E18, complete sequence," retrieved from EBI accession No. EMBL: AC112706, (Feb. 28, 2002).
XP002526200 "*Homo sapiens* chromosome 19 clone X200282, complete sequence," retrieved from EBI accession No. EMBL: AC092074, (Jun. 20, 2001).

* cited by examiner

*Primary Examiner*—Jehanne S Sitton
(74) *Attorney, Agent, or Firm*—Cantor Colburn LLP

(57) ABSTRACT

Provided is a polynucleotide for diagnosis or treatment of breast cancer, including at least 10 contiguous nucleotides of a nucleotide sequence selected from the group consisting of nucleotide sequences of SEQ ID No: 1 to SEQ ID No: 5 and comprising a nucleotide at $101^{st}$ position of the nucleotide sequence, or a complementary polynucleotide thereof.

3 Claims, No Drawings

POLYNUCLEOTIDE ASSOCIATED WITH BREAST CANCER COMPRISING SINGLE NUCLEOTIDE POLYMORPHISM, MICROARRAY AND DIAGNOSTIC KIT COMPRISING THE SAME AND METHOD FOR DIAGNOSING BREAST CANCER USING THE SAME

CROSS-REFERENCE TO RELATED PATENT APPLICATION

This application claims the benefit of Korean Patent Application No. 10-2005-0012038, filed on February 14, 2005, in the Korean Intellectual Property Office, the disclosure of which is incorporated herein in its entirety by reference.

BACKGROUND OF THE INVENTION

1. Field of the Invention

The present invention relates to polynucleotides associated with breast cancer, a microarray and a diagnostic kit comprising the same, and a method of diagnosing breast cancer.

2. Description of the Related Art

The genome of all organisms undergo spontaneous mutation in the course of their continuing evolution, generating variant forms of progenitor nucleic acid sequences (Gusella, Ann. Rev. Biochem. 55, 831-854 (1986)). The variant forms may confer an evolutionary advantage or disadvantage, relative to a progenitor form, or may be neutral. In some instances, some variant forms confer a lethal disadvantage and are not transmitted to subsequent generations of the organism. In other instances, some variant forms confer an evolutionary advantage to the species and are eventually incorporated into the DNA of most members of the species and effectively becomes the progenitor form. In many instances, both progenitor and variant form(s) survive and co-exist in a species population. The coexistence of multiple forms of a sequence gives rise to polymorphisms.

Polymorphisms include restriction fragment length polymorphism (RFLP), short tandem repeats (STR), variable number tandem repeat (VNTR), single nucleotide polymorphism (SNP), etc. Among these, SNP means a single nucleotide variant form of a polynucleotides present in an individual of the same species. When SNP occurs at coding region sequences, a defective or mutated protein may be expressed by any one of polymorphic forms. On the other hand, SNP may occur at non-coding region sequences. Some of these polymorphisms may result in the expression of defective or variant proteins (e.g., as a result of defective splicing). Other SNPs have no phenotypic effects.

It is known that in the case of a human, SNP occurs every about 300-1,000 bp. When the SNP influences on phenotype such as disease, a polynucleotide including the SNP can be used as a primer or a probe for diagnosing disease. A monoclonal antibody binding specifically to the SNP can also be used for diagnosis of disease and much research is being conducted on analyzing SNP and its function. The base sequence of SNP found in this way and other experimental results are stored in a free database.

Even though findings available to date show that specific SNPs exist on human genomes or cDNAs, phenotypic effects of such SNPs have not been revealed. Functions of most SNPs have not been disclosed yet except few SNPs.

Breast cancer can conventionally be diagnosed by x-ray, ultrasonic diagnosis, and biochemical and molecular biological methods. Among these methods, the molecular biological method cannot be used in an early diagnosis. It was identified by Myriad that about 3 to 30 SNP sites in genes BRCA1 and BRCA 2 are associated with breast cancer. However, most of these sites are used to identify genotypes of patients already diagnosed to have breast cancer and their prices are high. Thus, there is a need for a new SNP site associated with breast cancer.

SUMMARY OF THE INVENTION

The present invention provides polynucleotides including single nucleotide polymorphism (SNP) associated with breast cancer.

The present invention also provides a microarray or kit for diagnosing breast cancer including a polynucleotide including SNP associated with breast cancer.

The present invention also provides a method of diagnosing breast cancer.

According to an aspect of the present invention, there is provided a polynucleotide comprising at least 10 contiguous nucleotides of a nucleotide sequence selected from the group consisting of nucleotide sequences of SEQ ID No: 1 to SEQ ID No: 5 and comprising a nucleotide at position 101 of the nucleotide sequence, or a complementary polynucleotide thereof.

According to an aspect of the present invention, there is provided a polynucleotide hybridized with the polynucleotide of the present invention.

According to an aspect of the present invention, there is provided a microarray comprising the polynucleotide of the present invention.

According to another aspect of the present invention, there is provided a kit comprising the polynucleotide of the present invention.

According to another aspect of the present invention, there is provided a method of diagnosing breast cancer in an individual, the method comprising:

obtaining nucleic acid from the individual; and determining a nucleotide sequence of a polymorphic site ($101^{st}$ base) of at least one of polynucleotides of SEQ ID No: 1 to SEQ ID No: 5 or their complementary polynucleotides.

DETAILED DESCRIPTION OF THE INVENTION

The present invention provides a polynucleotide comprising at least 10 contiguous nucleotides of a nucleotide sequence selected from the group consisting of nucleotide sequences of SEQ ID No: 1 to SEQ ID No: 5 and comprising a nucleotide at position 101 of the nucleotide sequence, or a complementary polynucleotide thereof.

The polynucleotide comprises at least 10 contiguous nucleotides of a nucleotide sequence selected from the group consisting of nucleotide sequences of SEQ ID No: 1 to SEQ ID No: 5 and comprising a polymorphic site. The length of the polynucleotide is 10 to 400 nucleotides, and preferably 10 to 100 nucleotides, and more preferably 10 to 50 nucleotides. The polymorphic site is the $101^{st}$ position of each sequence.

The polynucleotides of SEQ ID No: 1 to SEQ ID No: 5 have polymorphic sequences. The polymorphic sequence refers to sequence including a polymorphic site having single nucleotide polymorphism (SNP) in a nucleotide sequence. The polymorphic site refers to a site at which SNP occurs in the polymorphic sequence. The polynucleotide may be DNA or RNA.

In the present invention, the polymorphic sites (101$^{st}$ base) in polymorphic sequences of SEQ ID No: 1 to SEQ ID No: 5 are associated with breast cancer. This can be identified by analyzing DNA sequences from blood samples of patients with breast cancer and normal persons. In the present invention, a case sample and a normal sample each include 300 persons who are divided into a group 40 or younger than 40 years old, a group 55 or older than 55 years old in consideration of menopause. The sizes of groups used in genotype analysis are indicated in the following table.

TABLE 1

| Age group | Normal (con.) | Patient (cas.) | Total |
|---|---|---|---|
| ≦40 | 90 | 87 | 177 |
| ≧55 | 90 | 96 | 186 |
| total | 300 | 300 | 600 |

Tables 2 and 3 illustrate the association of the polymorphic sequences of SEQ ID No: 1 to SEQ ID No: 5 with breast cancer and characteristics of the polymorphic sequences.

TABLE 2

| Marker | SNP | SEQ ID No: | Assay | | Allele frequency | | |
|---|---|---|---|---|---|---|---|
| | | | Method | Cas_Total | Con_Total | Cas_A2 | Con_A2 | Delta |
| SMBC_001 | [G/A] | 1 | Total sample | 288 | 299 | 0.285 | 0.339 | 0.054 |
| SMBC_025 | [T/C] | 2 | ≦40 | 83 | 87 | 0.319 | 0.448 | 0.129 |
| SMBC_035 | [G/A] | 3 | Total sample | 285 | 291 | 0.854 | 0.897 | 0.043 |
| SMBC_048 | [C/G] | 4 | ≧55 | 94 | 89 | 0.016 | 0.062 | 0.046 |
| SMBC_060 | [G/A] | 5 | Meta assay, total sample | 289 | 298 | 0.197 | 0.206 | 0.009 |

| Marker | Genotype frequency | | | | | |
|---|---|---|---|---|---|---|
| | Cas_A1A1 | Cas_A1A2 | Cas_A2A2 | Con_A1A1 | Con_A1A2 | Con_A2A2 |
| SMBC_001 | 152 | 108 | 28 | 128 | 139 | 32 |
| SMBC_025 | 41 | 31 | 11 | 27 | 42 | 18 |
| SMBC_035 | 12 | 59 | 214 | 3 | 54 | 234 |
| SMBC_048 | 91 | 3 | 0 | 78 | 11 | 0 |
| SMBC_060 | 186 | 92 | 11 | 187 | 99 | 12 |

| Chi-square (df = 2) | | Odds ratio: multiple model | | | HWE state | |
|---|---|---|---|---|---|---|
| Chi_value | Chi_exact_PValue | Risk allele | OR | CI | Cas_HW | Cas_HW |
| 6.01 | 4.95E-02 | A1 | A | 1.29 | (1.008, 1.654) | 1.949, HWE | .419, HWE |
| 6.139 | 4.64E-02 | A1 | C | 1.73 | (1.113, 2.696) | 2.056, HWE | .121 HWE |
| 6.452 | 3.97E-02 | A1 | A | 1.48 | (1.04, 2.113) | 8.265, HWD | .019, HWE |
| 5.439 | 2.53E-02 | A1 | G | 4.06 | (1.114, 14.81) | .5, HWE | .1, HWE |
| 0.165 | 9.21E-01 | A1 | A | 1.06 | (0.796, 1.408) | .011, HWE | .041, HWE |

TABLE 3

| Marker | Rs | Chr | Position | Band | Gene | Description | SNP role | a.a variation |
|---|---|---|---|---|---|---|---|---|
| SMBC_001 | rs1060442 | 19 | 836818 | 19p13.3 | THRAP5 | Thyroid hormone associated protein 5 | Coding-synon, Reference | No |
| SMBC_025 | rs3824414 | 9 | 125542902 | 9q33.3 | SLC2A8 | Solute carrier family 2, (facilitated glucose transporter) member 8 | Intron | No |
| SMBC_035 | rs10699 | 5 | 64902430 | 5q12.3 | TRIM23 | 23 containing tripartite motif | mma-utr, intron | No |
| SMBC_048 | rs5277 | 1 | 183887189 | 1q25.2–q25.3 | PTGS2 | Prostaglandin-endoperoxide synthase 2 (prostaglandin G/H synthase and cyclooxygenase) | Coding-synon, reference | No |
| SMBC_060 | rs2228480 | 6 | 152451086 | 6q25.1 | ESR1 | Estrogen receptor 1 | Coding-synon, reference | No |

In Tables 2 and 3, SMBC_025 is a marker found from a age group≦40 years old and SMBC_048 is a marker found from a group≧55 years old.

In Tables 2 and 3, the columns respectively have the following meanings.

SNP is a base of a SNP polymorphic site. Here, A1 and A2 represent respectively a low mass allele and a high mass allele as a result of experimental design according to a homogeneous MassEXTENSION™ (hME) technique (Sequenom) and are optionally designated for convenience of experiments.

SNP sequence represents a sequence containing a SNP site, i.e., a sequence containing allele A1 or A2 at position 101.

In the allele frequency column, cas_A2 refers to the frequency of allele A2 in a case sample, con_A2 refers to the frequency of allele A2 in a normal sample, and Delta refers to an absolute value of the difference between the cas_A2 and the con_A2. Cas_A2 is (the frequency of genotype A2A2× 2+the frequency of genotype A1A2)/(the number of sample of the case sample×2) and the con_A2 is (the frequency of genotype A2A2×2+the frequency of genotype A1A2)/(the number of sample of the normal sample×2).

The genotype frequency refers to the frequency of each genotype, in which cas_A1A1, cas_A1A2 and cas_A2A2 and con_A1A1, con_A1A2 and con_A2A2, respectively, denote the number of persons having genotypes A1A1, A1A2 and A2A2 in the case sample and the normal sample.

The chi-square (df=2) refers to the value of chi-square of which a degree of freedom is 2, in which the chi-value is the value of chi-square and a p-value is calculated based on the chi-value. The chi-exact-p-value refers to a p-value of Fisher's exact test of chi-square test. When the number of genotype is less than 5, the result of a general chi-square test may not be exact. Thus, the chi-exact-p-value is a variable used for more exact statistical significance (p-value) in Fisher's exact test. In the present invention, when p-value≦0.05, it is decided that the genotypes of the case sample and the normal sample are different from each other, i.e., there is a significant difference between the case group and the normal group.

In the risk allele, when the reference allele is A2, if the frequency of A2 in the case sample is greater than that of A2 in the normal sample (i.e., cas_A2 >con_A2), A2 is regarded as the risk allele, and in the opposite case, i.e., if the frequency of A1 in the case sample is greater than that of A1 in the normal sample (i.e., cas_A1>con_A1), A1 is regarded as the risk allele.

The odds ratio refers to the ratio of the probability of the risk allele in the case sample to the probability of the risk allele in the normal sample. In the present invention, a Mantel-Haenszel odds ratio method is used. CI denotes a 95% confidence interval of the odds ratio in the form of (lower limit, upper limit). When 1 falls under the confidence interval, it is considered that there is insignificant association of risk allele with disease.

The HWE state refers to the state of Hardy-Weinberg Equilibrium (HWE), in which the con_HWE and the cas_HWE denote the presence of HWE in the normal sample and the case sample, respectively. In the chi-square (df=1) test, when the chi-value is greater than 6.63 (p-value=0.01, df=1), it is decided to be Hardy-Weinberg Disequilibrium (HWD) and when the chi-value is less than 6.63, it is decided to be HWE.

Referring to Tables 2 and 3, the polymorphic markers of SEQ ID No: 1 to SEQ ID No: 5 of the present invention have chi-exact-p-value of 0.025 to 0.921 in 95% confidence interval as the result of the chi-square analysis between an expected value and an observed value of the allele frequency, indicating that all of the polymorphic markers are significantly different from the control group, and have the odds ratio of 1.06 to 4.06, indicating that they are associated with breast cancer.

SNPs of SEQ ID No: 1 to SEQ ID No: 5 of the present invention show significant appearance frequency differences in the case sample and the normal sample. Thus, the polynucleotide of the present invention can be effectively used for diagnosis and treatment of breast cancer, or gene fingerprinting analysis. Specifically, the polynucleotide can be used as a primer or a probe for diagnosis of breast cancer and as an antisense DNA or a composition for treatment of breast cancer.

The present invention also provides an allele-specific polynucleotide for diagnosis of breast cancer hybridized with the polynucleotide including at least 10 contiguous nucleotides of a nucleotide sequence selected from the group consisting of nucleotide sequences of SEQ ID No: 1 to SEQ ID No: 5 and comprising the nucleotide of a polymorphic site or a complementary polynucleotide thereof.

The allele-specific polynucleotide refers to polynucleotide hybridized specifically with each allele. That is, the allele-specific polynucleotide is hybridised such that a base of a polymorphic site in polymorphic sequences of SEQ ID No: 1 to SEQ ID No: 5 can be specifically distinguished. The hybridization can usually be carried out under a strict condition, for example, in a salt concentration of 1 M or less and at a temperature of 25° C. or higher. For example, 5×SSPE (750 mM NaCl, 50 mM Na phosphate, 5 mM EDTA, pH 7.4) and 25 to 30° C. may be suitable for the allele-specific probe hybridisation.

In the present invention, the allele-specific polynucleotide can be a primer. The primer refers to a single-strand oligonucleotide capable of initiating a template-directed DNA synthesis in an appropriate buffer under an appropriate condition (for example, in the presence of four different nucleoside triphosphates and a polymerizing agent such as DNA, RNA polymerase or reverse transcriptase) at a proper temperature. The length of the primer may vary according to the purpose of use, but is usually 15 to 30 nucleotides. A short primer molecule generally requires lower temperatures to be stably hybridized with a template. The primer sequence does not necessarily need to be completely complementary with the template, but should be sufficiently complementary to be hybridized with the template. Preferably, the primer has 3' end arranged so as to correspond to the polymorphic sites ($101^{st}$ bases) of SEQ ID No: 1 to SEQ ID No: 5. The primer is hybridised with a target DNA including the polymorphic site and initiates amplification of allele having complete homology to the primer. The primer is used as a primer pair with the other primer hybridized at the opposite side. Amplification is performed from the two primers, indicating that there is a specific allele. The primer of the present embodiment includes a polynucleotide fragment used in a ligase chain reaction (LCR).

In the present invention, the allele-specific polynucleotide may be a probe. The probe refers to a hybridization probe, which is an oligonucleotide capable of binding sequence-specifically to a complementary strand of a nucleic acid. Such a probe includes a peptide nucleic acid introduced by Nielsen, et al., *Science* 254, 1497-1500 (1991). The probe of the present invention is an allele-specific probe. When a polymorphic site is located in DNA fragments derived from two members of the same species, the allele-specific probe is hybridized with the DNA fragment derived from one member but is not hybridized with the DNA fragment derived from the other member. In this case, the hybridization condition should be sufficiently strict to be hybridized with only one allele by showing a significant difference in terms of the intensity of hybridization between alleles. The probe of the present invention is preferably arranged such that its central site (i.e., $7^{th}$ position in a probe consisting of 15 nucleotides, or $8^{th}$ or $9^{th}$ position in a probe consisting of 16 nucleotides) has the polymorphic site of the above sequence. In this way, a hybridization difference between alleles can be caused. The probe of the present invention can be used in a diagnosis method for detecting an allele, etc. The diagnosis method includes detection methods based on hybridization of nucleic acid such as southern blot. In a method using a DNA chip, the probe can previously be bound to a substrate of the DNA chip.

The present invention also provides a microarray including the polynucleotide of the present invention or a complementary polynucleotide thereof. The microarray may include a DNA or RNA polynucleotide. The microarray has the same structure as a conventional microarray, except that it includes the polynucleotide of the present invention.

The present invention also provides a kit including the polynucleotide of the present invention. The kit can include a reagent for polymerization, for example, dNTP, various polymerization enzymes, a colorizing agent, etc., in addition to the polynucleotide of the present invention. The kit can be used in diagnosis of breast cancer.

The present invention also provides a method of diagnosing breast cancer, the method including: obtaining nucleic acid from a individual; and determining a nucleotide sequence of a polymorphic site ($101^{st}$ base) of at least one polynucleotide selected from the group consisting of polynucleotides of SEQ ID No: 1 to SEQ ID No: 5 and their complementary polynucleotides. The method of diagnosing breast cancer may further include deciding that the risk of breast cancer is high when the nucleotide sequence of the polymorphic site is the same as at least one of risk alleles illustrated in Tables 2 and 3.

The obtaining of nucleic acid from an individual can be carried out by a conventional DNA isolation method. For example, nucleic acid can be obtained by amplifying a target nucleic acid through polymerase chain reaction (PCR) and purifying the amplified product. In addition, LCR (Wu and Wallace, $Genomics$ 4, 560 (1989), Landegren et al., Science 241, 1077 (1988)), transcription amplification (Kwoh et al., $Proc. Natl. Acad. Sci. USA$ 86, 1173 (1989)), self-sustained sequence replication (Guatelli et al., $Proc. Natl. Acad. Sci. USA$ 87, 1874 (1990)), and nucleic acid sequence based amplification (NASBA) can be used. Last two methods are associated with an isothermal reaction based on isothermal transcription and produce 30 or 100 times amplified single-strand RNA and double-strand DNA.

In an embodiment of the method, the determining nucleotide sequence of the polymorphic site includes hybridizing the nucleic acid sample onto a microarray on which a polynucleotide for diagnosis or treatment of breast cancer comprising at least 10 contiguous nucleotides selected from the group consisting of nucleotide sequences of SEQ ID No: 1 to SEQ ID No: 5 and comprising the nucleotide of the polymorphic site ($101^{st}$ base), or a complementary polynucleotide thereof, is immobilized; and detecting the hybridization result.

The method of preparing a microarray by immobilizing a probe polynucleotide on a substrate is well known in the art. The immobilization of the probe polynucleotide associated with breast cancer on a substrate can also be easily performed using a conventional technology. Also, the hybridization of nucleic acid on the microarray and the detection of the hybridisation result are well known in the art. For example, the nucleic acid sample is labelled with a fluorescent material, for example, a labelling material capable of generating detectable signals including Cy3 and Cy5, and then is hybridised on the microarray, followed by detecting signals generated from the labelling material.

In another embodiment, the method may further include determining that the individual belongs to a risk group having high probability of breast cancer when the determined nucleotide sequence of the polymorphic site corresponds to the at least one polymorphic site selected from the group consisting of SEQ ID No. 1 to SEQ ID No. 5 in which nucleotides of $101^{st}$ polymorphic sites are A, C, A, G and A, respectively. It can be determined that when many nucleic acid sequences having the risk allele are detected in an individual, the probability of belonging to a risk group is high.

The present invention will now be described in greater detail with reference to the following examples. The following examples are for illustrative purposes only and are not intended to limit the scope of the invention.

EXAMPLES

Example 1

DNA was isolated from blood of a case sample including breast cancer patients of 300people and a normal sample having group sizes as indicated in Table 1, and then an appearance frequency of a specific single nucleotide polymorphism (SNP) was analyzed. SNP in the present example was selected from the published database, either NCBI dbSNP or the REALSNP™ Assay Database of Sequenom Inc. A single nucleotide sequence in a sample was analyzed using a primer close to the selected SNP.

1. Preparation of DNA Sample

DNA was extracted from blood collected from the case sample and the normal sample. The DNA extraction was carried out according to a known extraction method (Molecular cloning: A Laboratory Manual, p 392, Sambrook, Fritsch and Maniatis, $2^{nd}$ edition, Cold Spring Harbor Press, 1989) and an indication of a commercially available kit (Gentra system). Only DNA having purity measured using UV (260/280 nm) of at least 1.7 was selected from the extracted DNA and used.

2. Amplification of a Target DNA

A target DNA having a certain DNA region including SNP to be analyzed was amplified using PCR. The PCR was performed in a general method and the conditions were as follows. 2.5 ng/ml of the target genome DNA was first prepared. Then, the following PCR reaction solution was prepared.

| | |
|---|---|
| Water (HPLC grade) | 2.24 μl |
| 10 × buffer (containing 15 mM MgCl$_2$, 25 mM MgCl$_2$) | 0.5 μl |
| dNTP mix (GIBCO) (25 mM/each) | 0.04 μl |
| Taq pol (HotStar) (5 U/μl) | 0.02 μl |
| Forward/reverse primer mix (1 μM/each) | 0.02 μl |
| DNA | 1.00 μl |
| Total reaction volume | 5.00 μl |

The forward and reverse primers were selected from upstream and downstream of SNP of the known database at proper positions. The primers were listed in Table 4.

Thermal cycling reaction was performed by maintaining at 95° C. for 15 minutes, 45 times cycling at 95° C. for 30 seconds, at 56° C. for 30 seconds and at 72° C. for 1 minute, and maintaining at 72° C. for 3 minutes, and then storing at 4° C. As a result, target DNA fragments having 200 nucleotides or less was obtained.

3. Analysis of SNP of the Amplified Target DNA

The analysis of SNP of the target DNA fragment was performed using homogeneous MassExtension (hME) technique of Sequenom. The principle of hME was as follows. First, a primer (extension primer) complementary to bases up to just before SNP of the target DNA fragment was prepared. The primer was hybridised with the target DNA fragment and a DNA polymerization was caused. At this time, a reagent (e.g. ddTTP) getting the polymerization to stop after adding base complementary to a first allele base (e.g. A allele) among the subject SNP alleles to the reaction solution was included. As a result, when the target DNA fragment included the first allele (e.g. A allele), a product having only one base complementary to the first allele (e.g. T) added was obtained. On the other hand, when the target DNA fragment included a second allele (e.g. G allele), a product having base complementary to the second allele (e.g. C) added and extended up to the nearest first allele base (e.g. A) was obtained. The length of the product extended from the primer was determined through mass analysis to determine the type of allele in the target DNA. Specific experimental conditions were as follows.

First, free dNTP was removed from the PCR product. For the purpose of this, 1.53 µl of pure water, 0.17 µl of HME buffer, and 0.30 µl of shrimp alkaline phosphate (SAP) were added to a 1.5 ml tube and mixed to prepare a SAP enzyme solution. The tube was centrifuged at 5,000 rpm for 10 seconds. Then, the PCR product was put into the SAP solution tube, sealed, maintained at 37° C. for 20 minutes and at 85° C. for 5 minutes, and then stored at 4° C.

Next, a homogeneous extension was performed using the target DNA product as a template. The reaction solution was as follows.

| | |
|---|---|
| Water (nanopure grade) | 1.728 µl |
| hME extension mix (10 × buffer containing 2.25 mM d/ddNTPs) | 0.200 µl |
| Extension primer (each 100 µM) | 0.054 µl |
| Thermosequenase (32 U/µl) | 0.018 µl |
| Total volume | 2.00 µl |

The reaction solution was mixed well and spin down centrifuged. The tube or plate containing the reaction solution was sealed and maintained at 94° C. for 2 minutes, 40 times cycled at 94° C. for 5 seconds, at 52° C. for 5 seconds and at 72° C. for 5 seconds, and then stored at 4° C. The obtained homogeneous extension product was washed with a resin (SpectroCLEAN™). The extension primers used for homogeneous extension were indicated in Table 4.

TABLE 4

Primers used for target DNA amplification and extension primers used for homogeneous extension

| Marker | Primer for target DNA amplification (SEQ ID No:) | | Extension primer (SEQ ID No:) |
|---|---|---|---|
| | Forward | Reverse | |
| SMBC_001 | 6 | 7 | 8 |
| SMBC_035 | 9 | 10 | 11 |
| SMBC_060 | 12 | 13 | 14 |
| SMBC_025 | 15 | 16 | 17 |
| SMBC_018 | 18 | 19 | 20 |

The obtained extension product was analyzed for the sequence of a polymorphic site using MALDI-TOF (Matrix Assisted Laser Desorption and Ionization-Time of Flight) among mass analysis methods. In the MALDI-TOF, if a material to be analysed was exposed to laser beam, it flew with an ionized matrix in vacuum state to a detector located at an opposite side. The flying time to the detector was calculated to analyze mass. For example, a material having low mass could rapidly reach the detector and a material having high mass could not rapidly reach the detector. The nucleotide of SNPs from one individual is calculated based on a difference in mass between the DNA fragments and known nucleotide sequences of the SNPs and determined.

The results of determining SNPs from individuals using the MALDI-TOF are indicated in Tables 2 and 3. Each allele may be in the form of homozygote or heterozygote in each individual. According to Mendel's principles of heredity and Hardy-Weinberg law, a compositional ratio of alleles composing a group is maintained at a constant frequency and when it is statistically significant, biological functional meaning can be given. The SNP of the present invention appears in patients with breast cancer at a statistically significant level as indicated in Tables 2 and 3, and thus it can be used for diagnosis of breast cancer, etc.

The polynucleotide of the present invention can be used for diagnosis and treatment of breast cancer and gene fingerprinting analysis.

The microarray or kit including the polynucleotide can effectively diagnose breast cancer.

The diagnosis method of breast cancer can effectively diagnose presence of breast cancer or risk.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of determining an increased risk of developing breast cancer in a human individual aged 55 years or older, the method comprising:
   obtaining nucleic acid from the individual; and
   determining in a nucleic acid sample from a human individual aged 55 years or older the nucleotide base at a polymorphic site at position 101 of SEQ ID No: 4, and
   determining the risk of developing breast cancer in the human individual aged 55 years or older, wherein determining the base is a G indicates an increased risk of developing breast cancer compared to determining the base is C.

2. The method of claim 1, wherein the operation of determining of the base of the polymorphic site comprises:
   hybridizing the nucleic acid sample onto a microarray on which is immobilized the polynucleotide comprising
   (a) at least 10 contiguous nucleotides of SEQ ID No. 4 comprising position 101, or
   (b) the complement of (a); and
   detecting the hybridization result.

3. The method of claim 2, wherein the polynucleotide or the complement of the polynucleotide has a length of 10 to 100 nucleotides.

* * * * *

SEQUENCE LISTING

<160> NUMBER OF SEQ ID NOS: 20

<210> SEQ ID NO 1
<211> LENGTH: 201

-continued

```
<212> TYPE: DNA
<213> ORGANISM: Homo sapiens
<220> FEATURE:
<221> NAME/KEY: variation
<222> LOCATION: (101)..(101)
<223> OTHER INFORMATION: r= G or A, polymorphic site

<400> SEQUENCE: 1
cagtgcttca ttccaagcct gccagcccac gtgatggcct cgcccgttc acctgctccg      60 acatgtcccg ggccaggaac ttgaggtggg tgatggcggg raacttgtcc ttgcggttga    120
ggtcggtggt gcagcgcatg aacagggagg gcaggatctc cgtgtcgata cggcacttct    180
cgctcaccac gctcacgcac a                                              201

<210> SEQ ID NO 2
<211> LENGTH: 201
<212> TYPE: DNA
<213> ORGANISM: Homo sapiens
<220> FEATURE:
<221> NAME/KEY: variation
<222> LOCATION: (101)..(101)
<223> OTHER INFORMATION: y = T or C, polymorphic site
<220> FEATURE:
<221> NAME/KEY: misc_feature
<222> LOCATION: (201)..(201)
<223> OTHER INFORMATION: n is a, c, g, or t

<400> SEQUENCE: 2
gtgaggcctt cagcaagagc tgcggcccac ggacatttgg tacccagcag ctgctgcgaa      60
gacgaccgtc ggggctgagg gttactcgct gctgcttctg ygccggtacc tcccatttcc    120
tcggcccaga gggtctgctc cgggaacttt ttgcagttcg ctgaggtcca aggcggggtg    180
gctgccaccc agtcagggct n                                              201

<210> SEQ ID NO 3
<211> LENGTH: 201
<212> TYPE: DNA
<213> ORGANISM: Homo sapiens
<220> FEATURE:
<221> NAME/KEY: variation
<222> LOCATION: (101)..(101)
<223> OTHER INFORMATION: r=G or A, polymorphic site

<400> SEQUENCE: 3
aaacagtaaa gagcacacat ttttatttac tcacaacact gaataattaa tgtaaacttt      60
ttgaattttt tttttcttta gacattttc ctctagagta rcttttcaag gccttctcat     120
gaacagcctt aagttttatt gtcaaaataa atgcacttat tttgggaaac agtttgaagt    180
aagtaataag catttgccac t                                              201

<210> SEQ ID NO 4
<211> LENGTH: 201
<212> TYPE: DNA
<213> ORGANISM: Homo sapiens
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: Variation
<222> LOCATION: (101)..(101)
<223> OTHER INFORMATION: s = G or C, polymorphic site

<400> SEQUENCE: 4
cttggaaata tgttttaga ttaggcttac agtattataa agcatatttt tctttgagaa       60
```

-continued

```
ngctaaaaac cttagaaaga cacttgtact tacatgtcaa sacataactc ataattgcat      120
ttcgaaggaa gggaatgtta ttcacaacgt tccaaaatcc cttgaagtgg gtaagtatgt      180
agtgcactgt gtttggagtg g                                                201
```

<210> SEQ ID NO 5
<211> LENGTH: 201
<212> TYPE: DNA
<213> ORGANISM: Homo sapiens
<220> FEATURE:
<221> NAME/KEY: variation
<222> LOCATION: (101)..(101)
<223> OTHER INFORMATION: r = G or A, polymorphic site

<400> SEQUENCE: 5

```
aggagacgga ccaaagccac ttggccactg cgggctctac ttcatcgcat tccttgcaaa       60
agtattacat cacggggag gcagagggtt tccctgccac rgtctgagag ctccctggct      120
cccacacggt tcagataatc cctgctgcat tttaccctca tcatgcacca ctttagccaa     180
attctgtctc ctgcatacac t                                                201
```

<210> SEQ ID NO 6
<211> LENGTH: 30
<212> TYPE: DNA
<213> ORGANISM: artificial sequence
<220> FEATURE:
<223> OTHER INFORMATION: primer

<400> SEQUENCE: 6

```
acgttggatg tatcgacacg gagatcctgc                                        30
```

<210> SEQ ID NO 7
<211> LENGTH: 30
<212> TYPE: DNA
<213> ORGANISM: artificial sequence
<220> FEATURE:
<223> OTHER INFORMATION: primer

<400> SEQUENCE: 7

```
acgttggatg aggaacttga ggtgggtgat                                        30
```

<210> SEQ ID NO 8
<211> LENGTH: 17
<212> TYPE: DNA
<213> ORGANISM: Artificial Sequence
<220> FEATURE:
<223> OTHER INFORMATION: primer

<400> SEQUENCE: 8

```
aaccgcaagg acaagtt                                                      17
```

<210> SEQ ID NO 9
<211> LENGTH: 30
<212> TYPE: DNA
<213> ORGANISM: artificial sequence
<220> FEATURE:
<223> OTHER INFORMATION: primer

<400> SEQUENCE: 9

```
acgttggatg aaggctgttc atgagaaggc                                        30
```

<210> SEQ ID NO 10
<211> LENGTH: 31
<212> TYPE: DNA
<213> ORGANISM: artificial sequence -continued

```
<220> FEATURE:
<223> OTHER INFORMATION: primer

<400> SEQUENCE: 10
acgttggatg cacaacactg aataattaat g                          31

<210> SEQ ID NO 11
<211> LENGTH: 19
<212> TYPE: DNA
<213> ORGANISM: artificial sequence
<220> FEATURE:
<223> OTHER INFORMATION: primer

<400> SEQUENCE: 11
atgagaaggc cttgaaaag                                        19

<210> SEQ ID NO 12
<211> LENGTH: 30
<212> TYPE: DNA
<213> ORGANISM: artificial sequence
<220> FEATURE:
<223> OTHER INFORMATION: primer

<400> SEQUENCE: 12
acgttggatg ttatctgaac cgtgtgggag                            30

<210> SEQ ID NO 13
<211> LENGTH: 30
<212> TYPE: DNA
<213> ORGANISM: artificial sequence
<220> FEATURE:
<223> OTHER INFORMATION: primer

<400> SEQUENCE: 13
acgttggatg catcgcattc cttgcaaaag                            30

<210> SEQ ID NO 14
<211> LENGTH: 18
<212> TYPE: DNA
<213> ORGANISM: artificial sequence
<220> FEATURE:
<223> OTHER INFORMATION: primer

<400> SEQUENCE: 14
gccagggagc tctcagac                                         18

<210> SEQ ID NO 15
<211> LENGTH: 30
<212> TYPE: DNA
<213> ORGANISM: artificial sequence
<220> FEATURE:
<223> OTHER INFORMATION: primer

<400> SEQUENCE: 15
acgttggatg aaaaagttcc cggagcagac                            30

<210> SEQ ID NO 16
<211> LENGTH: 30
<212> TYPE: DNA
<213> ORGANISM: artificial sequence
<220> FEATURE:
<223> OTHER INFORMATION: primer

<400> SEQUENCE: 16
acgttggatg ctgagggtta ctcgctgctg                            30
```

```
-continued

<210> SEQ ID NO 17
<211> LENGTH: 19
<212> TYPE: DNA
<213> ORGANISM: artificial sequence
<220> FEATURE:
<223> OTHER INFORMATION: primer

<400> SEQUENCE: 17
ggaaatggga ggtaccggc                                                  19

<210> SEQ ID NO 18
<211> LENGTH: 30
<212> TYPE: DNA
<213> ORGANISM: artificial sequence
<220> FEATURE:
<223> OTHER INFORMATION: primer

<400> SEQUENCE: 18
acgttggatg accttcgtgg tcttcaaacc                                       30

<210> SEQ ID NO 19
<211> LENGTH: 30
<212> TYPE: DNA
<213> ORGANISM: artificial sequence
<220> FEATURE:
<223> OTHER INFORMATION: primer

<400> SEQUENCE: 19
acgttggatg tacagtccct gagattctgc                                       30

<210> SEQ ID NO 20
<211> LENGTH: 20
<212> TYPE: DNA
<213> ORGANISM: artificial sequence
<220> FEATURE:
<223> OTHER INFORMATION: primer

<400> SEQUENCE: 20
tcaaaccgca ccccaagctc                                                  20
```